US 6,666,814 B2

(12) United States Patent
Downey et al.

(10) Patent No.: US 6,666,814 B2
(45) Date of Patent: Dec. 23, 2003

(54) ENHANCED INTRA-AORTIC BALLOON ASSIST DEVICE

(75) Inventors: H. Fred Downey, Fort Worth, TX (US); Cesar Diaz, Rancho Santa Margarita, CA (US)

(73) Assignee: PolyComp Services, Inc., Irvine, CA (US)

( * ) Notice: Subject to any disclaimer, the term of this patent is extended or adjusted under 35 U.S.C. 154(b) by 0 days.

(21) Appl. No.: 09/780,502

(22) Filed: Feb. 9, 2001

(65) Prior Publication Data

US 2001/0031907 A1 Oct. 18, 2001

Related U.S. Application Data

(63) Continuation-in-part of application No. 09/352,814, filed on Jul. 13, 1999, now Pat. No. 6,190,304.

(51) Int. Cl.$^7$ ................................................. A61M 1/10
(52) U.S. Cl. ................ 600/18; 604/102.03; 604/101.01
(58) Field of Search .................... 600/16–18; 604/96.01, 604/99.01, 101.01, 101.03, 101.05, 102.01, 102.03, 103.05; 623/3.1, 3.16, 3.21, 3.26, 3.28

(56) References Cited

U.S. PATENT DOCUMENTS

| 4,459,977 A | * | 7/1984 | Pizon et al. ................... 600/17 |
| 4,804,358 A | * | 2/1989 | Karcher et al. ............... 600/17 |
| 4,985,014 A | * | 1/1991 | Orejola ......................... 600/16 |
| 5,688,245 A | * | 11/1997 | Runge ......................... 604/151 |

* cited by examiner

*Primary Examiner*—Kennedy Schaetzle
(74) *Attorney, Agent, or Firm*—Charles D. Gunter, Jr.

(57) ABSTRACT

The present invention is an intra-aortic circulatory enhancing apparatus for use in human patients to improve blood flow to other arteries continuous with the aorta of the patient. The apparatus comprises an internal inflation means located within the aorta of the patient and an external inflation means located outside of the patient. The internal inflation means can be an internal balloon coupled to a hollow extent which is operatively coupled to a blood communication means. The blood communication means can be a first hollow catheter tube in one embodiment. The external inflation means can be an external balloon coupled to a hollow extent running through the center of the balloon and continuous with a second hollow catheter tube. The blood communication means is coupled to the internal and external inflation means, allowing blood within the aorta to communicate with the secondary inflation means.

6 Claims, 13 Drawing Sheets

ENHANCED INTRA-AORTIC BALLOON ASSIST DEVICE

CROSS REFERENCE TO RELATED APPLICATIONS

This application is a continuation-in-part of prior Ser. No. 09/352,814, filed Jul. 13, 1999, entitled "Enhanced Intra-Aortic Balloon Assist Device", now U.S. Pat. No. 6,190,304.

BACKGROUND OF THE INVENTION

1. Field of the Invention

The present invention relates generally to intra-aortic balloon pump type devices ("IABP") that act as a left ventricular assist devices ("LVAD") as well as to related devices which assist in maintaining a patient's cardiac output when the normal cardiac output is not sufficient to maintain an adequate pressure for supplying the patient's organs with arterial blood.

2. Description of the Prior Art

The intra-aortic balloon pump ("IABP") is by far the most commonly utilized left ventricular assist device ("LVAD"). This device is used when the patient's cardiac output is not sufficient to maintain an adequate arterial blood supply to the patient's organs.

The IABP consists of an inflatable balloon attached to a catheter, which is advanced through the patient's femoral artery and into the descending aorta. Inflation and deflation of the balloon is accomplished by an external control unit synchronized with the heart beat. This unit rapidly inflates the balloon during the diastolic or resting phase of the heart cycle, and thus elevates diastolic aortic blood pressure and improves blood flow to the heart, the brain and other tissues. The balloon is rapidly deflated as the heart contracts. This reduces the aortic blood pressure that the heart must overcome to eject blood from the left ventricle. Thus, the IABP is a LVAD that also augments diastolic aortic blood pressure.

However, present IABP devices cannot sustain the circulation if the heart is severely diseased or injured, since ventricular ejection must be sufficient to keep the mean aortic blood pressure above approximately 60 mmHg. When the aortic pressure falls below this value, there is insufficient blood to fill the space around the balloon when it is deflated. In that case the wall of the aorta collapses around the deflated balloon of prior art devices, and the IABP becomes ineffective. Thus, present IABP devices can be used only in less severe cases of left ventricular failure.

In one aspect, the present invention is directed towards improving the usefulness of IABP devices by enhancing the use of a single balloon in the descending aorta with a second, external balloon located outside the body and in direct communication with the blood within the aorta through a hollow catheter tube connecting both balloons. Although several IABP devices have used multiple balloons to enhance circulation, none use an external balloon working cooperatively with the internal balloon. Gabbay (U.S. Pat. No. 4,527,549) discloses the use of a balloon within the ascending aorta and multiple smaller balloons within the aortic arch and descending aorta. Given the difficulty in positioning a balloon within the ascending aorta with a catheter coming up from the descending aorta, the Gabbay device is cumbersome and difficult to operate. More importantly, the Gabbay device has the disadvantage of being positioned in the ascending aorta in order to function, thus increasing the chance of producing emboli that can cause problems such as stroke. Choy et al. (U.S. Pat. No. 4,902,273) discloses a dual balloon device, but which operates by a completely different mode. In the Choy et al. device, one balloon enters the left ventricle of the heart and another balloon enters the right ventricle of the heart. In a diseased heart, which may already be dilated, this would excessively expand the ventricle and may cause rupture or other permanent damage. Positioning the balloons in that invention is also cumbersome, making the device impractical for many applications.

In another aspect of the present invention, an internal catheter, rather than an internal balloon, cooperates with an external balloon located outside the body and in direct communication with the blood in the aorta.

Both aspects of the invention are intended to address the need for a device of the above type that has greater pumping capacity, that is simple to use and capable of rapid insertion and operation in an emergency situation, and that is capable of elevating blood pressure within the ascending aorta even if the descending aorta should collapse. The present invention is directed towards such a device or devices.

SUMMARY OF THE INVENTION

One object of the present invention is to provide a means and method for enhancing heart function when the blood pressure within the aorta is insufficient to prevent the collapse of the descending aorta around an intra-aortic balloon.

Another object of the present invention is to enhance the blood flow to the heart, brain, and other tissues under the conditions of poor heart function.

Another object of the present invention is to provide a means for enhancing the pumping and sucking effect of an IABP within the aorta by using a simple, unitary device that is self contained and easy to use.

Yet another object of the present invention is to provide a means of enhancing the perfusion of other arteries such as the renal arteries and the aortic arch arteries.

Yet another object of the present invention is to provide a device that acts cooperatively through a continuous unit, the size of which can be varied to adapt to the size of the patient or the desired amount of pumping.

These objects are achieved in the present invention by an intra-aortic circulatory enhancing apparatus for use in human patients to improve blood flow to other arteries continuous with the aorta of the patient. The apparatus comprises an internal inflation means located within the aorta of the patient and an external inflation means located outside of the patient. The internal inflation means can be an internal balloon coupled to a hollow extent which is operatively coupled to a blood communication means. The blood communication means can be a first hollow catheter tube in one embodiment. The external inflation means can be an external balloon coupled to a hollow extent running through the center of the balloon and continuous with a second hollow catheter tube. The blood communication means is coupled to the internal and external inflation means, allowing blood within the aorta to communicate with the secondary inflation means. Further, a pressurization means for pressurizing and depressurizing the internal and external balloons is provided. The pressurization control means is a lumen in one embodiment of the invention, the lumen associated with the balloons and extending from the balloons to be coupled to an external control unit. When operating, the balloons pump simultaneously, then draw or suck blood simultaneously, thus helping to generate blood flow. The balloons pressurize and depressurize simultaneously, thus acting cooperatively to enhance the blood-pumping action of a diseased human heart and enhance blood flow to the heart, brain, and other tissues.

In another embodiment of the invention, the external balloon itself communicates with the blood communication means. The external balloon is located within a relatively rigid sheath or housing so that by alternately applying pressure and vacuum to the interior of the housing, the external balloon can be acted upon to thereby either draw or suck blood into the blood communication means and into the external balloon.

In other embodiments of the invention, the upper balloon is merely a retaining balloon which helps to position and retain a perforated catheter, the perforations serving as the entry points for blood entering the blood communication means and leading to the external inflation means.

Additional objects, features and advantages will be apparent in the written description which follows.

DETAILED DESCRIPTION OF THE INVENTION

Apparatus.

One embodiment of the present invention utilizes an internal inflation means in the form of an inflatable balloon in the descending aorta similar to that of present IABP devices, but has additional cooperative pumping capacity. This additional capacity is provided by an external inflation means, in the present embodiment an inflatable balloon, in a chamber outside the body. The internal and external inflation means are not limited to being in the form of a balloon, but can take other forms consistent with the function of pumping and sucking blood to and from the aorta of the patient under conditions of poor heart function.

Figure 1:
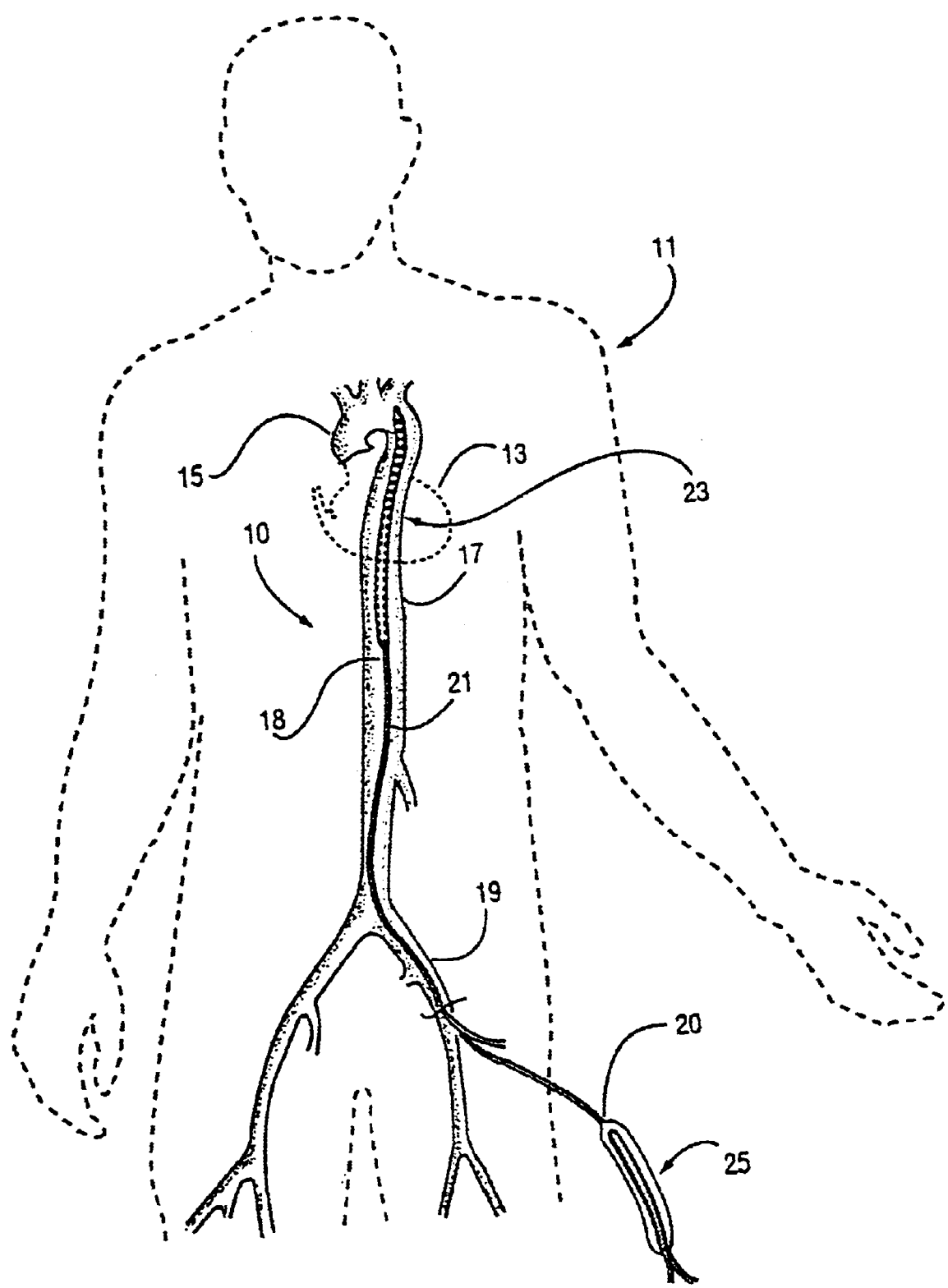
FIG. 1 is a fanciful view of portions of the human body and the apparatus of the invention inserted therein.

The present invention is first described with reference to FIG. 1, wherein the apparatus 10 is a continuous unit that is reversibly implanted into patient 11 having heart 13, ascending aorta 15, and descending aorta 17. Within the patient is the internal inflation means 23, and outside the patient is external inflation means 25. The inflation means in the present embodiment are balloons coupled to hollow extents running through the center of the balloons, the balloons being made from a flexible and nonthrombogenic material. The hollow extents are made from rigid and flexible material, as will be described more fully. Although the hollow extent is described as running through the center of the internal balloon, the balloon and extent can also be placed in other configurations consistent with the invention. The two inflation means 23 and 25 communicate through the tube assembly 21 having a proximal end 18 and distal housing end 20.

Figure 2:
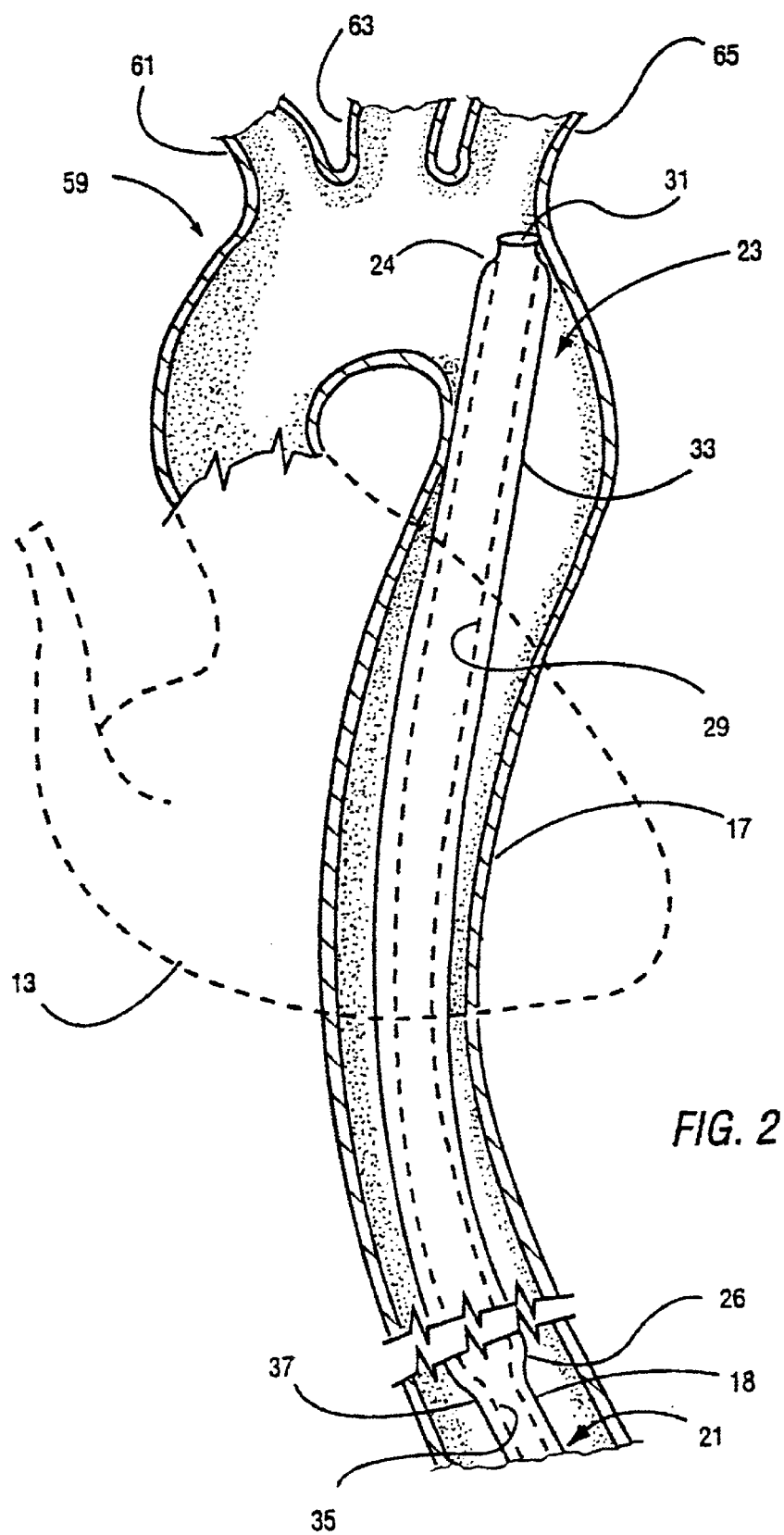
FIG. 2 is an exploded, detailed view of the internal inflation means of the invention.
Figure 3:
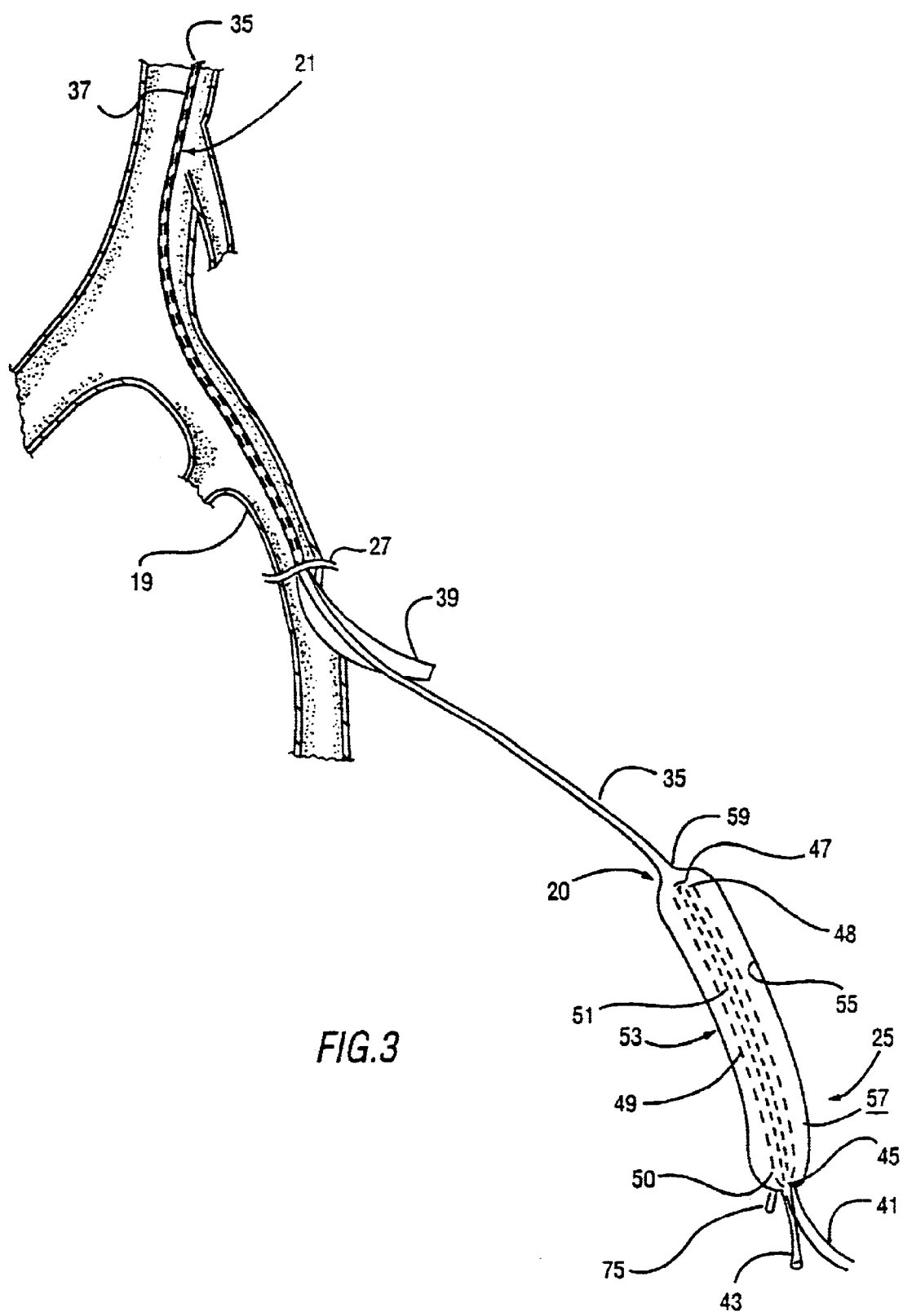
FIG. 3 is an exploded, detailed view of the external inflation means of the invention.
Figure 4:
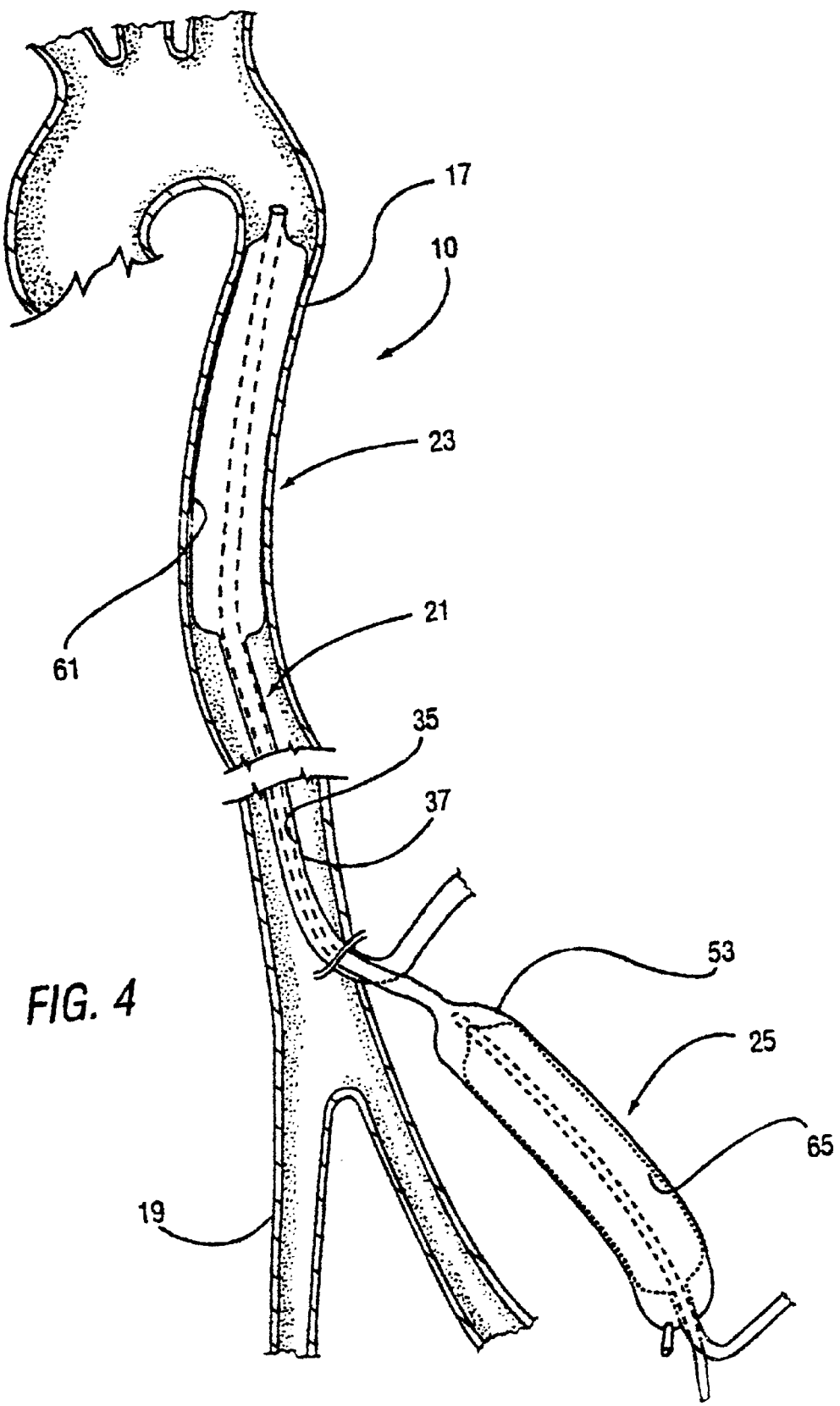
FIG. 4 is an exploded, cutaway view of the apparatus in the patient in the pressurized position.

The further description of the apparatus is best understood with reference to the placement in the patient's body. A surgical incision 27 (FIG. 3) is made in the patient 11 such that the internal inflation means 23 can be inserted first into the femoral artery 19, and up into the descending aorta 17. The internal inflation means 23 is pushed up into the aorta by applying force upon the tube assembly 21 which is rigid and flexible. Referring to FIGS. 2–4 the tube assembly is further described. The tube assembly 21 comprising first hollow catheter tube 35 and first lumen 37. The first hollow catheter tube 35 serves as a blood communication means in the present embodiment although other tube or channel creating structures are appropriate for the passage of blood. The first hollow catheter tube 35 is continuous with the hollow extent 29, thus allowing blood to flow through to opening 31 and in communication with the aorta of the patient. The first hollow catheter tube 35 is made from a rigid yet flexible material that is formed into a tube having a hollow interior continuous with its length.

As will be explained more fully, the hollow extent 29 of the first hollow catheter tube 35 communicates the aorta with an external pumping chamber as a means for transferring blood from the aorta to the external pumping chamber. Since hollow extent 29 and catheter tube 35 are relatively small in cross section as compared to the aorta, they can cause resistance to high flow rates in operation of the device. It is therefore desirable to reduce the possibility of hemolysis during high volume pumping such as in the left ventricular assist mode of operation of the device. In order to improve the fluid carrying capacity of the extent 29 of the internal balloon and catheter tube 35 as well as the remainder of the blood transport system of the device, the interior surfaces thereof are preferably constructed of low coefficient of friction materials such as PTFE, polyamides, FEP, PFA or similar materials. The preferred class of materials are characterized by having a coefficient of friction equal to that of PTFE (polytetrafluroethylene) or no greater than about ten times that of PTFE.

The inner surfaces of the blood carrying portions of the device can also have coatings of or be chemically bonded to polymers which provide a lubricious effect. Polymers useful for such applications include the general class of materials listed above as well as known hydrophilic/hydrophobic substances. Such substances are known in the art of catheter manufacture for making the external surfaces of catheters slick. However, the application of such substances in the present device is aimed at reducing the resistance to flow within the blood carrying passages of the device so that large volumes of blood can be displaced through the catheter interior with a minimal hemolysis effect. The coatings of the invention, in addition to providing increased lubricity, can also be modified to reduce coagulation and transmission of infection from the environment to the body. This could be accomplished by incorporating antibacterial substances such as benzylchromium, silver based chemicals or equivalent antibacterial substances into the polymers.

In addition to the lubricious coatings applied to the inner surfaces of the blood carrying portions of the device, it may be desirable to coat the outer surfaces of the internal inflating means with low coefficient of friction materials which promote the infusion and removal of gas from the interior of the balloon.

As will be described more fully, the hollow extent 29 of the catheter tube 35 is stressed during the inflation and deflation of the balloon. Under high volume/high frequency pumping circumstances, the inner extent 29 is slightly enlarged and then slightly compressed. These stresses can give rise to deformation of the inner extent 29 of the catheter 35 that acts as the blood transfer line for the external pumping chamber of the device. Such stresses are undesirable. In some cases, when the external pumping device is actuated, the internal conduits may develop an "S" type bend due to flexing, causing the catheter to stretch and recoil. This action can cause a snap or hammer effect in the pumping action of the device unless additional design criteria are employed.

In order to address these aspects of the operation of the device, it is preferred that the internal catheter and extent 29 be stabilized during blood transfer and also during balloon inflation. This can be accomplished by constructing the inner extent 29 of a laminate type structure so that a thin wall metal tube can be lined or coated to form a lubricious surface as described above. The outside of the tube can be covered with a material that can be bonded by means of heat fusion, chemical bonding or suitable adhesives to the balloon and other catheter components as well as sub-system components.

The internal catheter 35 and extent 29 can also be reinforced by having a center portion of the wall thickness formed of composite structure which, instead of featuring a metal tube, utilizes a coil or braid of wire of high tensile strength material that provides stiffness and dimensional stability. In addition, the metal reinforcement could be provided in the form of a single or multi-wire material which extends from the proximal end of the catheter to the distal end thereof which has sufficient stiffness to maintain the catheter straight and stable under normal use.

A pressurization means is provided to pressurize the internal inflation means. The pressurization means preferably includes a continuous tube, lumen, or tube-like structure that starts from the distal end 26 of balloon 33 and extends a length along the first hollow catheter to allow pressurizing gas to enter and exit the internal balloon 33. The internal balloon 33 in FIG. 2 is shown in a partially pressurized state in going to the pressurized state as shown in FIG. 4. In the present embodiment shown in FIG. 2, the pressurization means is first lumen 37. The lumen is continuous with the first hollow catheter tube 35, and operatively coupled to the internal balloon 33.

The first hollow catheter tube 35 extends into the internal balloon through extent 29, the extent terminating at opening 31. This opening allows blood within the aorta to communicate through extent 29 into the length of the first hollow catheter tube 35, and ultimately to the external inflation means described further infra. The internal balloon has a proximal end 24 and a distal end 26, the proximal end typically placed in the descending aorta 17 near the aortic arch 59.

Tube assembly 21 couples the internal and external inflation means and allows blood communication from the aorta to the external inflation means 25. External inflation means 25 is described with reference to FIG. 3. Extending from the distal end 26 of internal inflation means 23, the tube assembly 21 extends through the descending aorta and into the femoral artery, exiting the patient 11 at incision 27, coupling with the external inflation means 25. The first lumen 37 extends away from the first hollow catheter 35 to form first pressurization tube 39.

First hollow catheter tube 35 extends outside the patient to form catheter housing 53, the housing having an internal wall 55 that forms pumping chamber 57. The catheter tube 35 can extend most any length from the internal inflation means 23 to the external inflation means 25, the length from proximal end 18 to distal end 20 depending on the size of the patient. Thus, the apparatus 10 can be made to various sizes to be used on patients of various sizes, from small children to larger adults.

Within the chamber 57 is the external pumping balloon 49, the external balloon being coupled to a second hollow catheter tube 43. The balloon 49 is shown in FIG. 3 in a partially pressurized state in going to the fully pressurized state of FIG. 4. Extending through the center of the balloon is extent 51, which forms a sensor opening 47. The extent 51 is continuous with the catheter tube 43, thus allowing a pressure sensor to be coupled to the catheter tube 43 for sensing the blood pressure within chamber 57. The sensor opening 47 is located at the proximal end 48 of external balloon 49, the distal end 50 of balloon 49 narrowing to second lumen 45. The second lumen 45 then exits the housing 53 to form pressurization tube 41. The internal walls 55 are of a diameter such as to allow the external balloon 49 to pressurize until it fills the volume of chamber 57.

In addition to the conduits, tubes or lumens for conducting the pressurized gas, the pressurization means also includes a mechanical pressurization means for inflating and deflating (pressurizing and depressurizing) the balloons of the invention. The mechanical pressurization means is connected to the balloons by means of first pressurization tube 39 and second pressurization tube 41. Pressurization tubes 39, 41 extend a length to be coupled to an external control unit (38 in FIG. 7), the unit being designed to supply a gas such as helium to the balloons of the invention. The gas is pressurized to inflate the balloons into a pumping position, and depressurized to deflate the balloons into a sucking position. Thus, blood is pumped and drawn to facilitate the heart's function. Second hollow catheter tube 43 can be used to inject substances into the patient and to couple to a pressure sensing device located external to the patient. The pressure sensor would measure the change in pressure within chamber 57 during systole and diastole of the left ventricle.

The pumping action of the balloons is controlled by an electrocardiogram, wherein the detected depolarization of the heart muscles (contraction) triggers the external control unit to depressurize and deflate those balloons. The external control unit is programmed by the user to automatically trigger the inflation of the balloons when the heart muscle relaxes.

Figure 7:
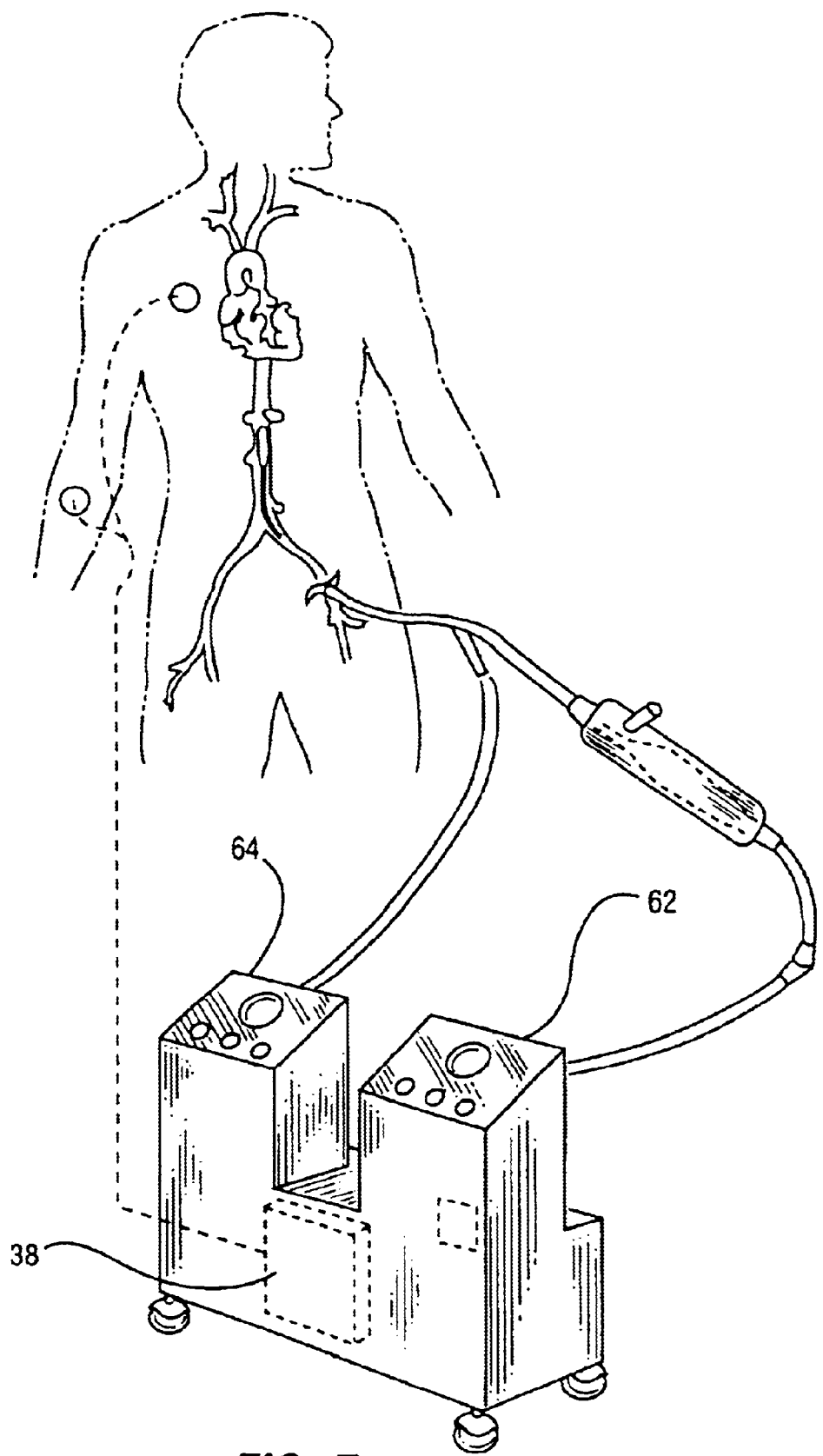
FIG. 7 is a schematic view of the two independent pumps used to deliver pressurized gas and vacuum to different portions of one device or multiple devices of the invention.

FIG. 7 shows a particularly preferred form of the mechanical pressurization means of the invention. In the embodiment of the device of FIG. 7, two independent pumps 62, 64 are provided which are capable of delivering pressurized gas/vacuum to different portions of one device, i.e., pressurization tubes 39, 41 in FIG. 3, and/or multiple devices. The pumps 62, 64 are triggered by specific events related to the QRS complex of heart function. It is not necessary that the triggering event be tied to the "R" event and, in fact, any event in the QRS complex can be utilized. The pumps are preferably designed for independent control to allow different pressures and flow rates for the intended application. The dual pump arrangement illustrated in FIG. 7 is especially well adapted for use with the device of the invention since the pumping requirements for the internal balloon and the pumping requirements for the external balloon are significantly different. The external pumping requirements are typically several times, i.e., five times the requirements for the internal inflation means. The dual pump arrangement easily accommodates such requirements.

Although the pumps 62, 64 are independently adjustable and operable, it will be understood that the pumps could also be synchronized to augment and supplement the heart action, as well. Also, although a dual stage pump assembly is illustrated, multiple stage pump assemblies are also envisioned with the pump stages operating either in sequence or out of sequence, the pumps being independently adjustable and operable based upon one biological model obtained through the ECG and QRS complex of the patient.

Operation.

The mode of operation of the apparatus is now described with respect to the embodiments of the invention shown in FIGS. 1–4. Once the internal inflation means 23 is in position within the aorta, blood is allowed to purge into the first catheter 35 through opening 31. The blood is communicated down the length of the catheter 35 into chamber opening 59 and filling chamber 57. As blood enters and fills chamber 57, air within chamber 57 escapes through one-way air valve 75. The air valve 75 is coupled to the housing 53, preferably close to the position of the pressurization tube 41 on housing 53. A one-way air valve is common and its design and use is understood by those skilled in the art.

During systole, the left ventricle contracts and expels blood into the aorta. At this stage, the external control unit is triggered by the electrocardiogram to depressurize the internal balloon 33 and external balloon 49, thus deflating these balloons. The deflated balloons increase the volume within the aorta 17 and chamber 57. This has the effect of drawing or sucking blood into the descending aorta surrounding the internal inflation means 23 and into the opening 31 and down to chamber opening 59, thus filling the volume of chamber 57.

The balloons of the invention are next pressurized (inflated) by the external control unit, the timing set after a preselected time period following deflation as described supra. Gas flows into lumens 39 and 41 and into external balloon 49 and internal balloon 33, simultaneously pressurizing both balloons. When balloon 33 is pressurized and thus inflated, the volume within the aorta that surrounds the balloon is filled with the balloon material, thus decreasing the volume and forcing blood around the balloon 33 either towards the aortic arch or towards the distal aorta. When balloon 49 is pressurized, the space within chamber 57 is filled with the balloon material. This pushes blood that is within the chamber 57 out chamber opening 59 and into the first hollow catheter tube 35, up to opening 31 and out into the aorta.

FIG. 4 shows the pressurized position of the apparatus 10. The internal balloon is in the fully pressurized (inflated) state 61, while the external balloon is in the fully pressurized (inflated) state 63. As can be seen in FIG. 4, the space surrounding the internal and external balloons is filled by the balloons in the pressurized state, thus decreasing the volume within the aorta 17 and catheter housing 53, respectively. This forces blood away from the balloons to create the pumping action.

The level of pressurization of the internal and external balloons can be controlled by the pressurization means coupled to the external control unit. The degree of inflation can also be controlled by the operator wherein the external control means is set to deliver/withdraw a predetermined amount of gas to and from the balloons. This allows for varying volumes of blood to be delivered through the hollow catheter tube 21 to the aorta of the patient. Also, the external balloon can be independently controlled to allow for various volumes of blood to be delivered to the aorta. Specifically, the external control means can be set by the user to inflate the balloon 49 at a certain level, thus filling chamber 57 to varying degrees. Thus, if the balloon 49 is only partially inflated at its most pressurized state, then chamber 57 will only be partially filled by the balloon, thus delivering a lower volume of blood than could be delivered if the balloon 49 were inflated to its maximum level to fill the chamber 57 completely. This offers the advantage of delivering varying amounts of blood, depending on the size of the patient and/or nature of the heart's condition.

The external control unit rapidly inflates the balloons during the diastolic or resting phase of the heart cycle, and thus elevates diastolic aortic blood pressure and improves blood flow to the heart, brain, and other tissues. The balloons of the invention are rapidly deflated as the heart contracts, thus producing a sucking effect that draws blood from the left ventricle and the ascending aorta. This reduces the aortic blood pressure that the heart must overcome to eject blood from the left ventricle. Thus, the apparatus 10 of the present invention is a LVAD that also augments diastolic aortic blood pressure.

Figure 5:
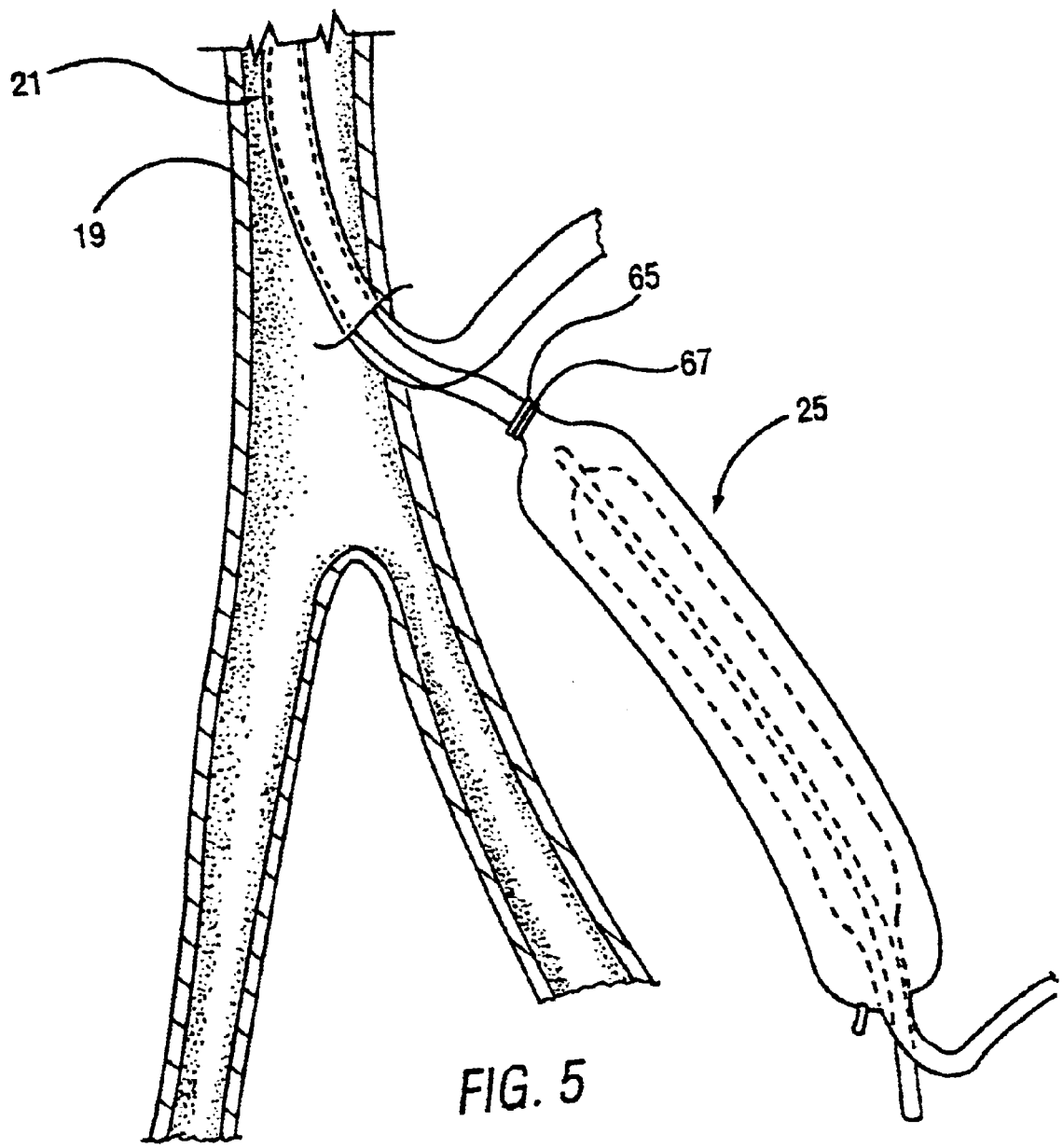
FIG. 5 is an exploded view of the coupling means of the invention.

The pumping and sucking action of the apparatus 10 of the present invention supplies blood to other arteries such as the brachiocephalic trunk 61 (FIG. 2), left common carotid artery 63, left subclavian artery 65, and renal arteries. Further, the apparatus can be tailored to fit the individual patient. The apparatus can be made from two parts that can be separated and changed out to allow different sized internal inflation means to be coupled to different sized external inflation means. This is described with reference to FIG. 5, wherein a coupling means comprising two mating couplers. A coupler 65 is attached to one end of the tube assembly 21 associated with the internal inflation means 23, and the coupler 67 is attached to an end section of the tube assembly 21 associated with the external inflation means 25. The couplers 65 and 67 can be female and male threaded joints, pressure sensitive joints, or other joints wherein the hollow catheter tube 35 endings make intimate contact with one another so that a firm seal is made for pressurized blood within the catheter to flow uninterrupted.

The size of the internal pumping balloon can be varied depending on the patient size, while the external balloon size can be varied by taking into account such variables as the desired volume defined by chamber 57, thus either increasing or decreasing the volume of blood delivered to the patient. The size of the internal pumping balloon can be independently chosen to fit various sized external pumping balloons, a means being provided to change out one sized internal balloon with another for a given external balloon, and vice versa.

Specifically, the diameter of the tube assembly 21 can be made in many sizes to allow the medical practitioner that is treating the patient to choose from a variety of sizes to fit the size of the patient. The outside diameter of the tube assembly 21 is similar to the inner diameter of the patient's femoral artery 19. This relatively large diameter allows rapid and efficient movement of blood between the ascending aorta 15 and the external inflation means 25. The external balloon 49 located in the pumping chamber 57 will be deflated and inflated at the same time as the internal balloon, and both balloons will be operated by an external control unit, similar to that of the present IABP. Thus, deflation of the balloon in the pumping chamber will further lower aortic pressure during left ventricular ejection. Should the aortic systolic pressure be so low that the walls of the aorta contract around the internal balloon, deflation of the balloon in the pumping chamber will still withdraw blood from the ascending aorta, since the walls of the pumping chamber are rigid. Further, the tube assembly 21 is rigid and made wide enough so that a passage for blood remains even if the aorta collapses around the internal inflation means 23. Operation of the external inflation means 25 will pump and suck blood into and out of the aorta even if the pumping action of the internal inflation means 23 is ineffective. Thus, the external inflation means 25 will augment, or in severe conditions, supplant the action of the internal inflation means.

Figure 6:
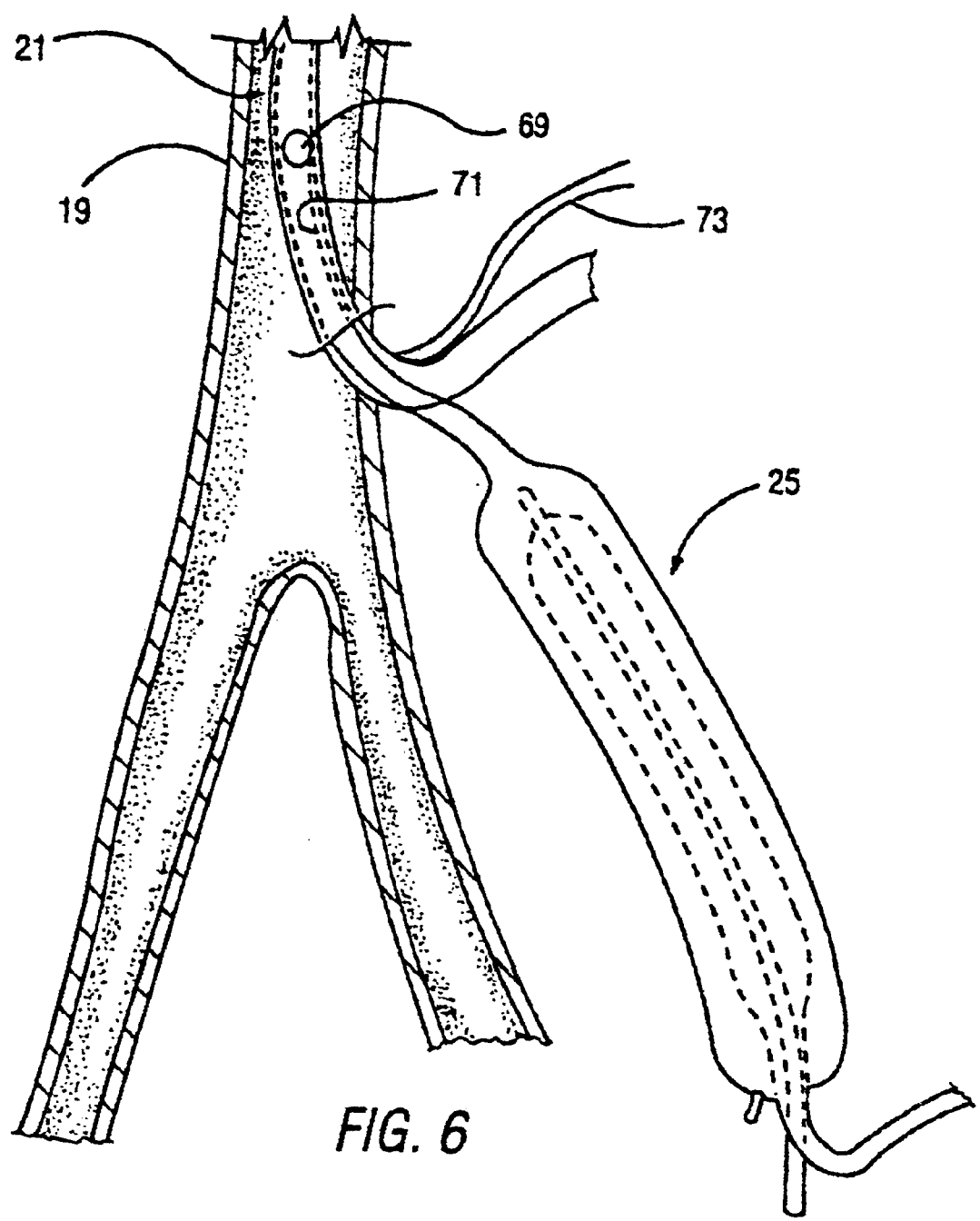
FIG. 6 is an exploded view of the perfusion eyelet of the invention.

In another embodiment of the present invention shown in FIG. 6, the tube assembly 21 has a perfusion eyelet 69. The perfusion eyelet is an opening into the hollow catheter tube 35 that allows communication of blood between the tube 35 and the surroundings within the aorta. The perfusion eyelet 69 has an open and a closed position, the opening and closing being controlled by a donut-shaped balloon surrounding the opening of the eyelet. The eyelet operates much like the iris of an eye, wherein the donut-shaped balloon is fabricated to allow for the closing of the opening upon inflation without obstructing the lumen of the tube assembly 21.

The donut-shaped balloon can be pressurized to close the opening, thus not allowing blood communication between the aorta and first hollow catheter tube 35, and depressurized to hold the eyelet open, thus allowing blood communication. A separate lumen 71 and pressurization tube 73 continuous therewith is provided for inflating and deflating the donut-shaped balloon. The eyelet would preferably be located at a region of the tube assembly 21 within the descending aorta once the apparatus is in place within patient 11. The position of the eyelet 69 in FIG. 6 is for illustration only and is not intended to limit its actual position along tube assembly 21. The perfusion eyelet would allow perfusion of the kidneys through the left and right renal arteries even if the descending aorta collapses around the internal balloon. During deflation of balloon 49, the eyelet would also facilitate the entry of blood into chamber 57 by allowing blood from the descending aorta to enter the eyelet and travel down the catheter tube 35 to fill chamber 57.

Other Embodiments.

Figure 8:
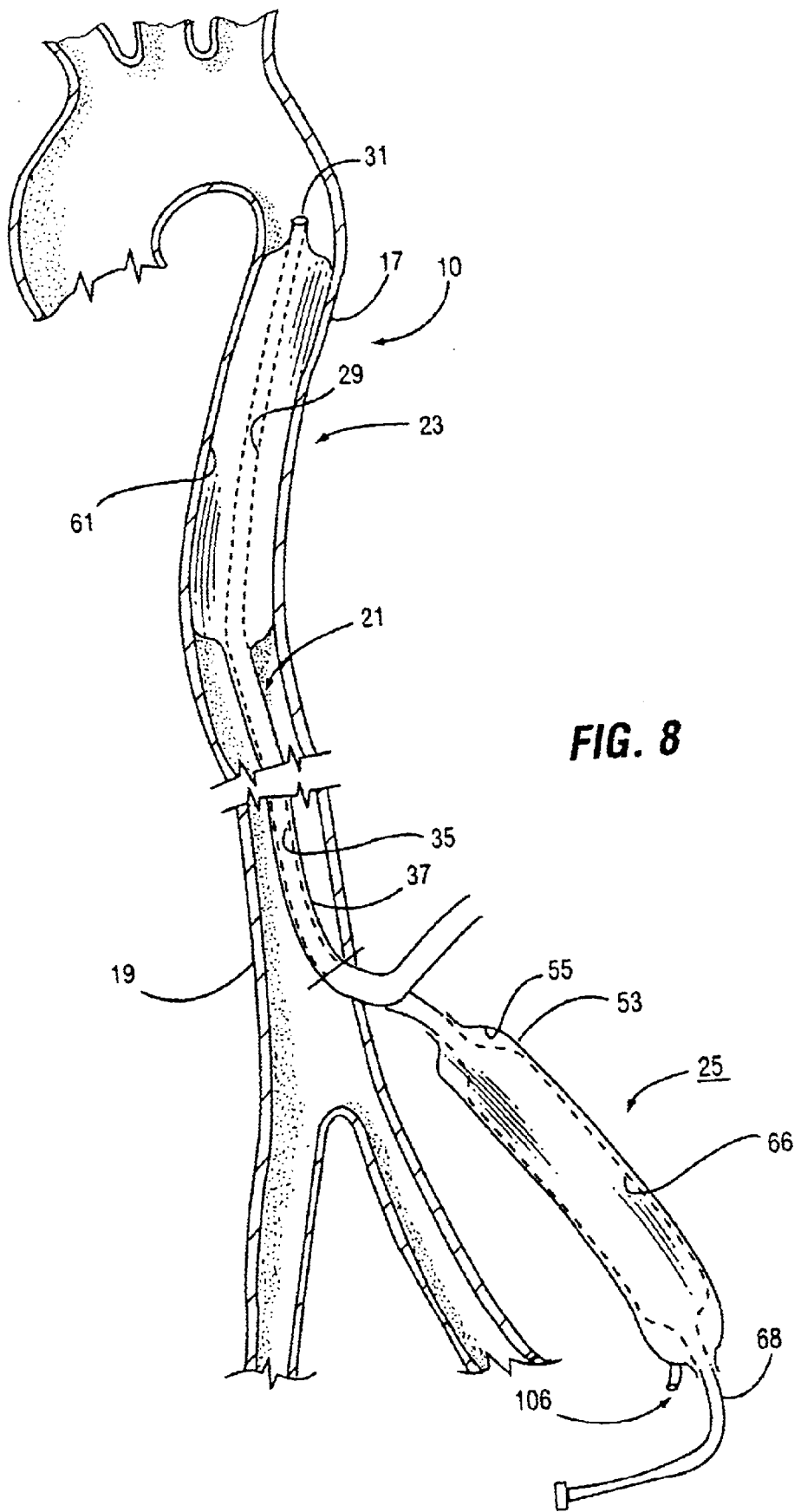
FIG. 8 is a view similar to FIG. 4 but showing a rigid external housing for the external balloon, the external force being applied to the housing interior to act upon the external balloon.

FIG. 8 shows another embodiment of the invention. In the embodiment of FIGS. 1–6, blood enters the opening 31 in the internal balloon extent 29 and travels to the chamber 55 located in the external inflation means 25. Chamber 55 has gas pressure added and removed by means of port 106 in order to achieve the inflation and deflation of the balloon 49, thereby drawing blood from the aorta as well as pushing blood into the aorta. By making the housing 53 of the lower inflation means 25 of a rigid or semi-rigid material, a "shell" is formed which uniformly and consistently contains the blood for accurate displacement into the patient's body during pumping. By providing an outer housing of a rigid construction, the chamber 53 is now capable of being used both a pressure chamber and a vacuum chamber.

In the embodiment of FIG. 8, the housing 53 is constructed of a rigid or semi-rigid material so that blood entering the opening 31 can enter the interior 66 of the of the external balloon. The different path of travel ensures that the blood being transferred never contacts transfer lines, edges or joints of materials other than the inner surface of the balloon and the transfer line, which components can be made to behave or act more nearly as one assembly. The device of FIG. 8 can also be provided with an IV line 68 at either end of the balloon for introducing drugs or other substances into the blood stream. The totally "in-line" design would allow the device to accept additional tools, for example, a catheter or guiding device for purposes of pump supported angioplasty and/or stent delivery, as well as drug therapy.

Figure 9:
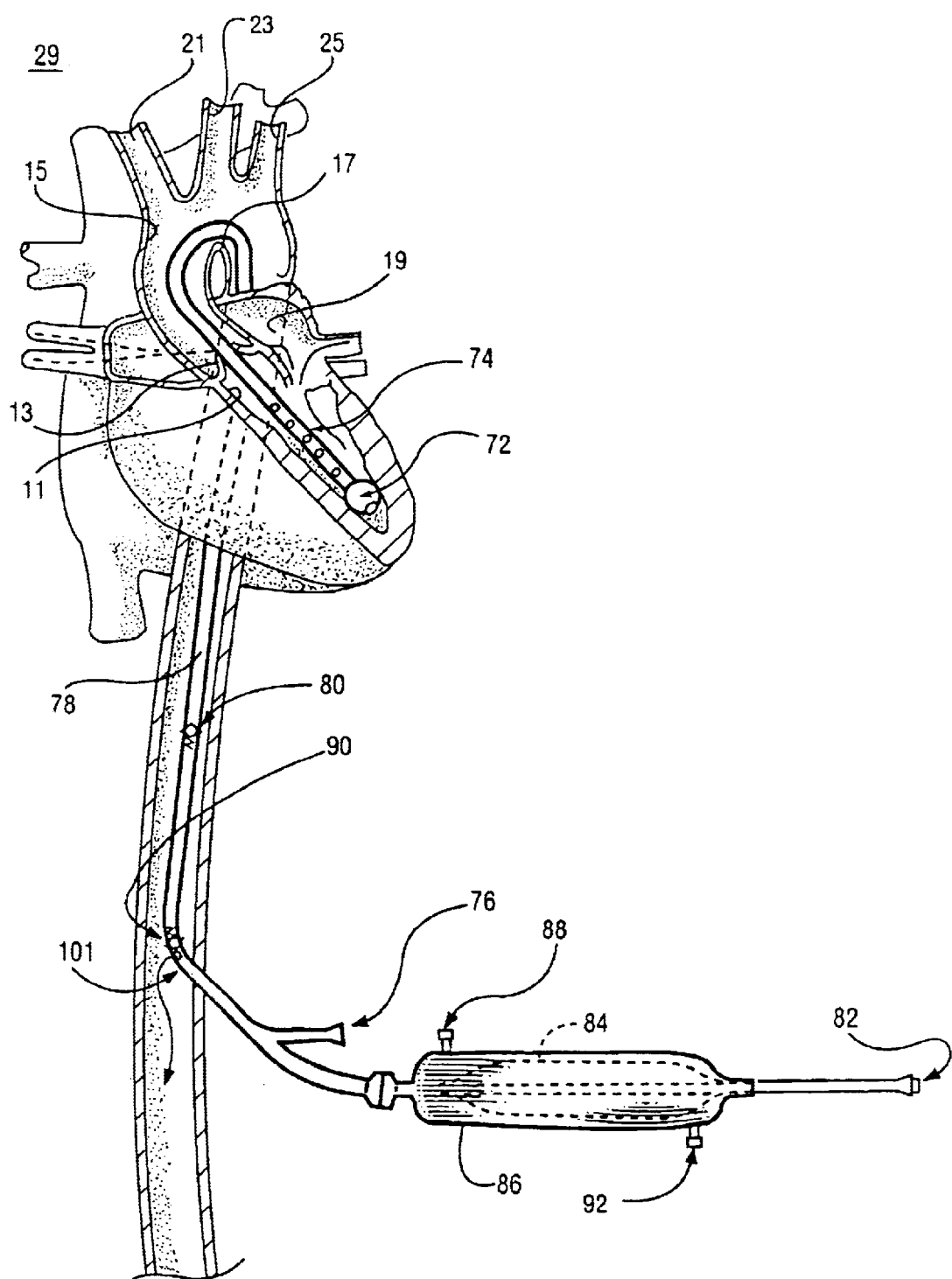
FIG. 9 is another embodiment of the invention in which the internal balloon is replaced by a perforated catheter which is held in place by an internal retaining balloon.

FIG. 9 shows another embodiment of the invention in which the internal balloon is replaced by a simple retaining balloon 72 and a perforated catheter section 74. The section 74 can be provided with a single large fluid port or a plurality of fluid ports on the side of the catheter. The retaining balloon 72 is inflated by means of lumen 76 in the same manner as previously described with respect to the pressurization tubes (39, 41, in FIG. 3). The catheter section 74 is placed inside the left ventricle and draws blood from the ventricle to unload the ventricle. Blood is moved through the tubing section 78 and through the one way check valve 80 in the direction of the external inflating means. The one way check valve 80 opens under vacuum and closes under pressure so that blood passing through the valve cannot return in the direction of the ventricle.

Gas pressure and vacuum are alternately applied through the inlet 82 to inflate and deflate the external balloon 84 which is housed within the relatively rigid sheath or housing 86. A pressure probe 88 can be used to monitor the pressurization cycle. A second one way check valve 90 operates oppositely from valve 80, i.e., valve 90 opens under pressure and closes with a vacuum. This allows fluid ejection through the valve port or opening 101 in the direction of the lower part of the ascending aorta or other desired location. In the arrangement of FIG. 9, the heart continues to pump blood, thereby reducing problems associated with the collapsing of an internal balloon. An IV line can be connected to the port 92 in order to introduce drugs or other agents into the blood surrounding the external balloon 84 within the housing 86.

Figure 10:
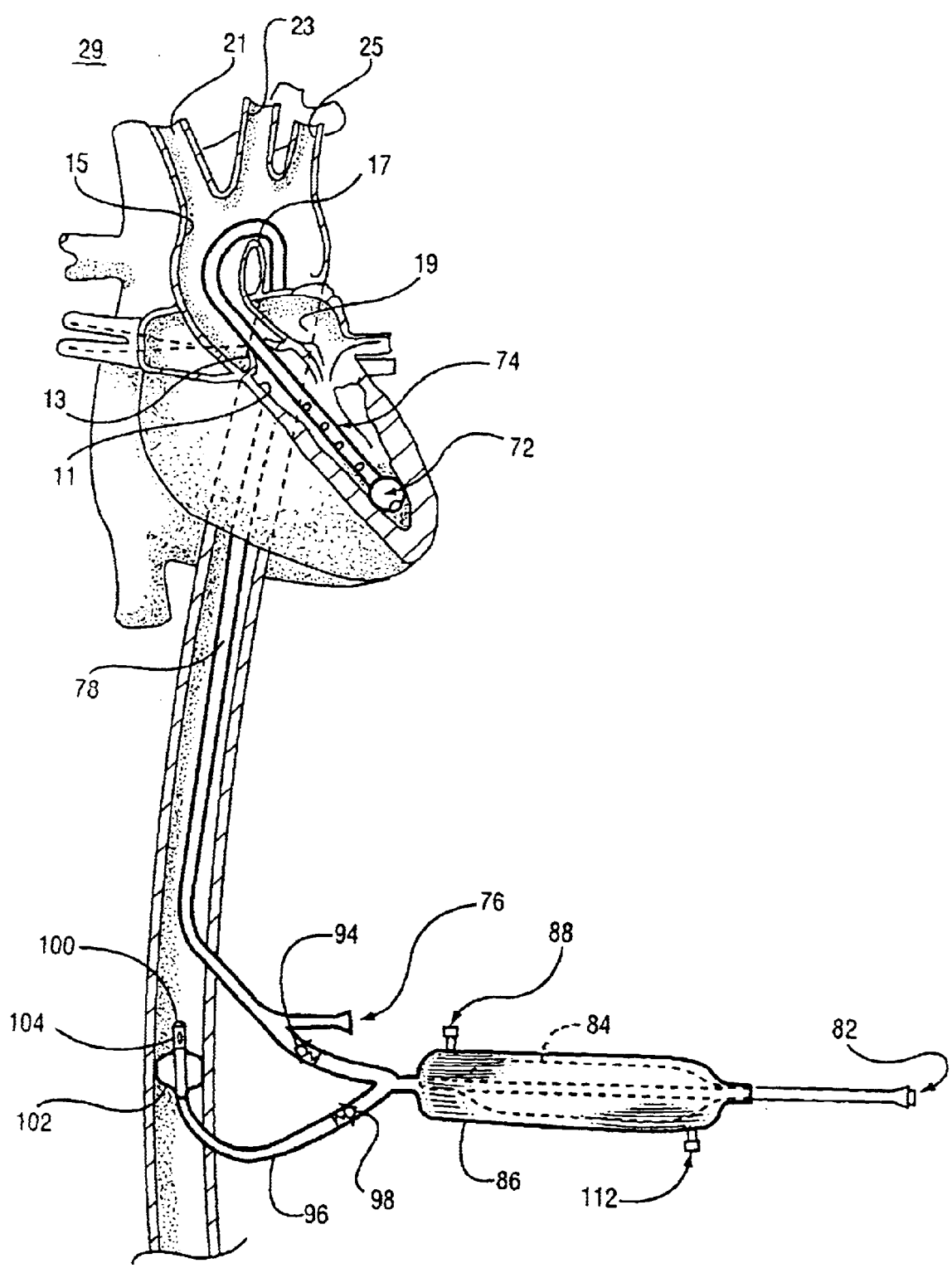
FIG. 10 is a view similar to FIG. 9 showing an alternate valving arrangement.

FIG. 10 shows another arrangement for routing the flow of blood from the perforated catheter section 74. In this arrangement, blood passing through the tubing 78 passes through a one way check valve 94 to the interior of the external balloon housing 86. Another branch of tubing 96 containing a check valve 98 allows the flow of blood to an infusion port 100 but restricts flow in the opposite direction. The perfusion port 100 is maintained in position, for example by a retaining balloon 102, or other convenient means. A safety side port 104 can also be present. In the arrangement of FIG. 9, the reinjected blood could flow from the fluid ejection port 101 in the direction of the lower extremities. In the embodiment of FIG. 10, however, blood is forced in the direction of the brain and heart. It is also possible to install the infusion mechanism 100 below the renal artery, or in other locations as well.

Figure 11:
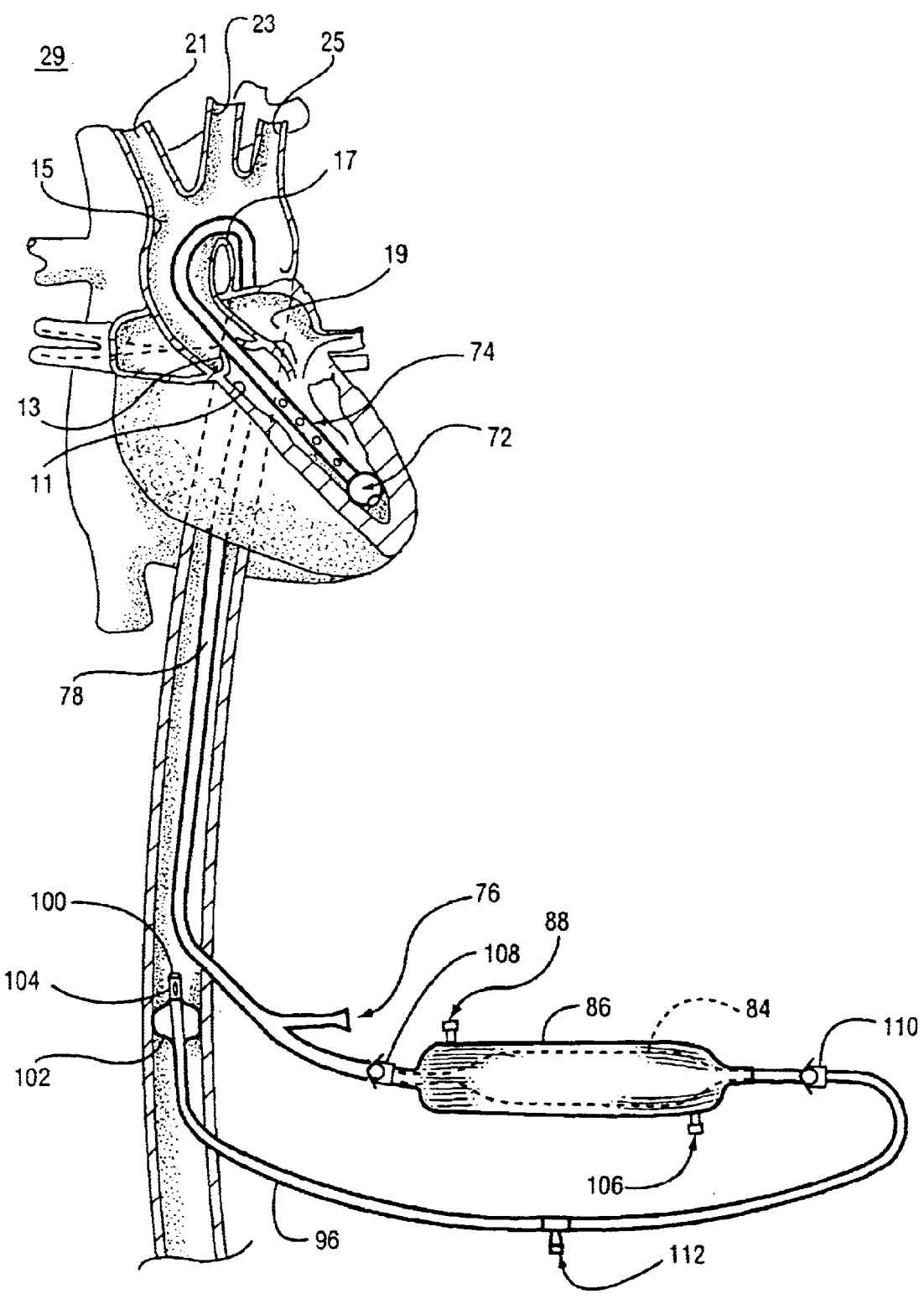
FIG. 11 is a view similar to FIG. 10 but with the blood flow passing through the external balloon and pressure being applied to the external balloon housing.

FIG. 11 shows another embodiment of the invention, similar to FIG. 10, in which the external pumping mechanism is essentially reversed. That is, the external balloon 84 is connected in-line with the tubing 78 and with exit tubing 96 with the external sheath or housing 86 being pressurized by means of a port 106. Check valve 108 allows blood to be drawn from the tubing 78 to the interior of the housing 86 but prevents flow in the opposite direction. Check valve 110 located on the opposite side of the housing 86 similarly allows the flow of blood from the pressurized housing 86 in the direction of the infusion port 100. An IV connection 112 can be provided for injecting drugs or other agents into the blood stream.

Figure 12:
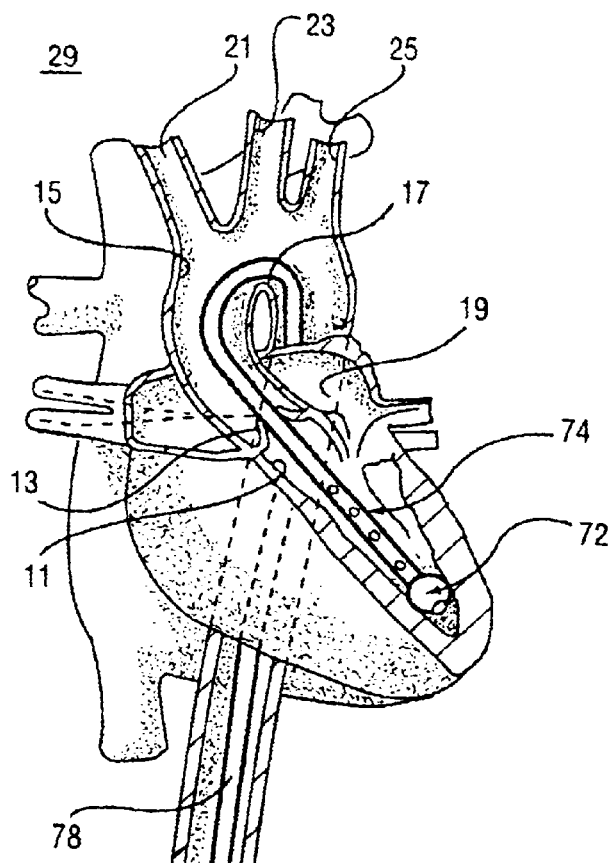
FIG. 12 is a view similar to FIG. 11 but showing the incorporation of auxiliary blood treatment equipment into the blood flow through the system.
Figure 12:
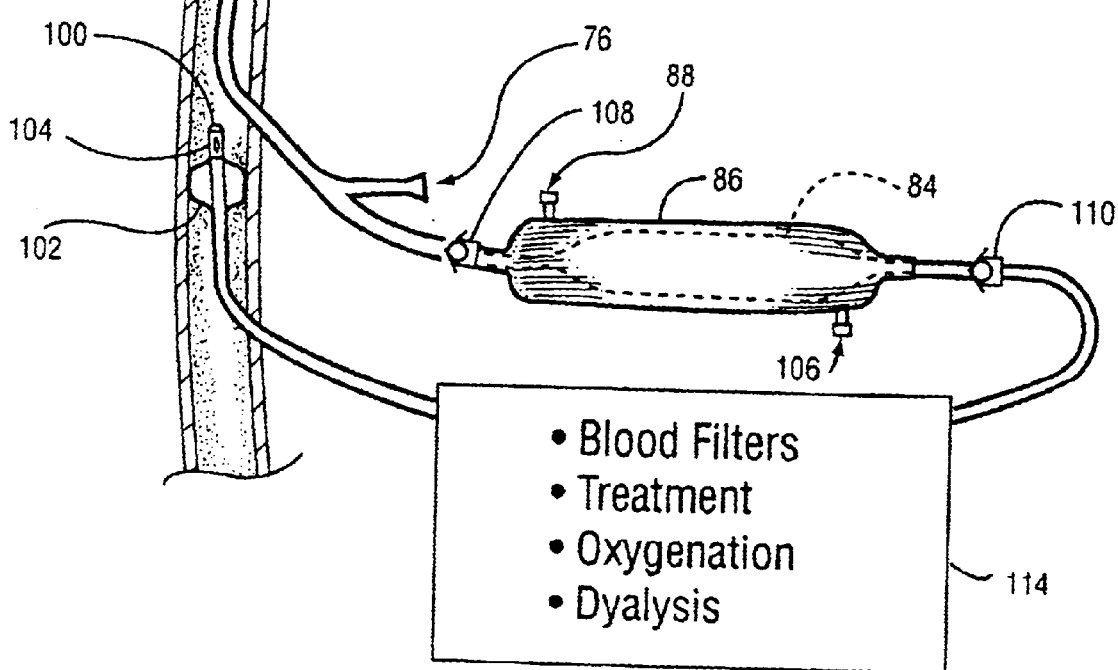

FIG. 12 shows another embodiment of the invention essentially utilizing the device of FIG. 11. However, instead of the simple IV inlet 112, FIG. 12 schematically illustrates the presence of various auxiliary blood treatment systems 114. Thus, instead of utilizing a simple IV connection, the pressurized blood can be directed to the filtering components of a blood treatment system, for example for hemodialysis. If desired, the blood could be oxygenated at this point in the system by providing the appropriate oxygenation equipment.

Figures 13, 14:
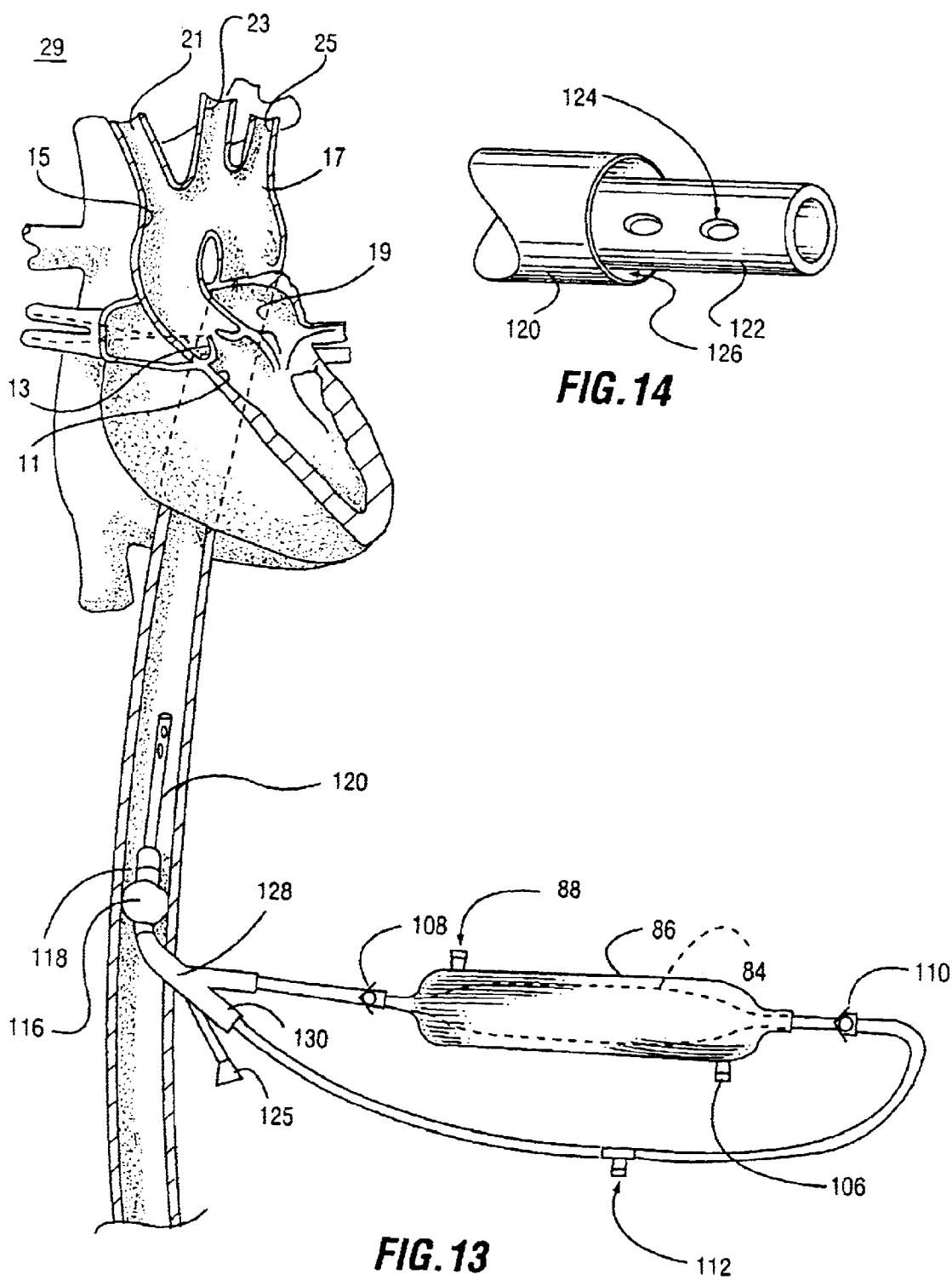
FIG. 13 is another embodiment of the invention in which an occlusion balloon is used to block the flow of blood to the lower extremities.
FIG. 14 is an enlarged view of the catheter portion of the device of FIG. 13.

FIG. 13 shows another embodiment of the invention in which an occlusion balloon 116 is placed within the ascending aorta. The occlusion balloon 116 includes a side port 118 for infusion and also includes a stem region 120. As shown in greater detail in FIG. 14, the stem region 120 includes an inner elongated extent 122 provided with a plurality of infusion ports, 124 the annular region between the inner extent 122 and the outer stem 120 comprising a suction port or region 126.

The external balloon pump is arranged in essentially the same configuration as that shown in FIG. 12 with the external balloon 84 being in communication with the blood entering the tubing 128. Blood exiting the external balloon pump and passing through the check valve 110 is routed back through tubing branch 130 to be reinfused through side port 118 and infusion ports 124 at the region above the occlusion balloon 116. This arrangement blocks the flow of blood to the lower extremities and introduces blood in front of the occlusion balloon 116.

Advantages.

One advantage of the first device of the invention lies in the ability of the apparatus to pump and suck blood within the descending aorta even when the aorta collapses. The tube assembly is rigid yet flexible, and of a diameter such that if the aorta collapses around the internal balloon, it does so only to the extent that the tube assembly will allow. The tube assembly, having the hollow catheter tube and coupled to the hollow extents, creates a channel through which blood can communicate with the external balloon. Thus, the external balloon can pump and suck blood if the internal balloon is ineffectual.

Another advantage of the various forms of the device lies in the external balloon itself. The arrangement of the external balloon with the internal balloon allows an enhanced pumping and sucking action. Thus further enhances circulation of blood to the ascending aorta and other aortic arteries.

Yet another advantage of the invention in its various forms is its simplicity. The apparatus is a singular, unitary design that essentially resides in one housing that can be inserted into a patient's femoral artery and up to the descending aorta, a common medical procedure. This will allow the apparatus to be used in emergency situations, and more easily in all situations. The apparatus can be made from two parts that can be separated and changed out to allow different sized internal inflation means to be coupled to different sized inflation means.

Yet another advantage of the present invention is the ability to optionally eject blood into the descending aorta to improve renal blood flow.

Yet another advantage of the present invention is the ability to vary the pumping capacity of the apparatus including the use of a dual pump system for individually pressurizing the internal and external pressurization means.

Yet another advantage of the apparatus is that the placement of the external balloon. The external balloon is placed external from the patient yet in communication with the blood. This allows for more space within the aorta for the internal components and fewer internally placed foreign objects, thus reducing the chances of a thrombogenic reaction.

While the invention has been shown in several of its forms, it is not thus limited but is susceptible to various changes and modifications without departing from the spirit thereof.

What is claimed is:

1. An intra-aortic circulatory enhancing apparatus for use in a human patient to improve the function of a weak or diseased heart, the apparatus comprising:

an internal catheter terminating at one extent in a retaining balloon, the internal catheter having a perforated region for receiving blood flow into an interior of the catheter, the internal catheter extending to an opposite extent to form a blood conveying tube;

an external housing in communication with the blood conveying tube and an external balloon residing within the external housing;

a pressurization means for alternately pressurizing and applying vacuum to the external balloon, thereby alternately drawing blood and pumping blood to and from the external housing;

wherein the internal catheter is for placement within a left ventricle of the human and the external balloon is located outside of the patient; and wherein the blood conveying tube includes a first check valve which opens under vacuum and closes under pressure and a second check valve located in the direction of the external housing which opens under pressure and closes under a vacuum.

2. An intra-aortic circulatory enhancing apparatus for use in a human patient to improve the function of a weak or diseased heart, the apparatus comprising:

an internal catheter terminating at one extent in a retaining balloon, the internal catheter having a perforated region for receiving blood flow into an interior of the catheter, the internal catheter extending to an opposite extent to form a blood conveying tube;

an external housing having an interior in communication with the blood conveying tube and an external balloon residing within the interior of the external housing;

a pressurization means for alternately pressurizing and applying vacuum to the external balloon, thereby alternately drawing blood and pumping blood to and from the external housing;

wherein the internal catheter is for placement within a left ventricle of the human and the external balloon is located outside of the patient;

wherein the blood conveying tube includes a first check valve which opens under vacuum and closes under pressure and a second check valve located in the direction of the external housing which opens under pressure and closes under a vacuum; and wherein a fluid injection port is located below the second check valve.

3. The apparatus of claim 2, wherein an external port communicates with the housing interior for supplying desired agents to the blood located within the housing interior.

4. The intra-aortic circulatory enhancing apparatus of claim 2, wherein the pressurization means for alternately pressurizing and applying vacuum to the external balloon comprises a multiple stage pumping apparatus.

5. An intra-aortic circulatory enhancing apparatus for use in a human patient to improve the function of a weak or diseased heart, the apparatus comprising:

an internal catheter terminating at one extent in a retaining balloon, the internal catheter having a perforated region for receiving blood flow into an interior of the catheter, the internal catheter extending to an opposite extent to form a blood conveying tube;

an external housing in communication with the blood conveying tube and an external balloon residing within the external housing;

a pressurization means for alternately pressurizing and applying vacuum to the external balloon, thereby alternately drawing blood and pumping blood to and from the external housing;

wherein the internal catheter is for placement within a left ventricle of the human and the external balloon is located outside of the patient;

wherein the pressurization means for alternately pressurizing and applying vacuum to the external balloon comprises a multiple stage pumping apparatus; and wherein the pressurization means comprises a dual action pumping apparatus having separate pumping sections for the internal retaining balloon and for the external balloon, thereby accommodating differing pumping requirements for the internal retaining balloon and the external inflation balloon.

6. An intra-aortic circulatory enhancing apparatus for use in a human patient to improve the function of a weak or diseased heart, the apparatus comprising:

an internal catheter terminating at one extent in a retaining balloon, the internal catheter having a perforated region for receiving blood flow into an interior of the catheter, the internal catheter extending to an opposite extent to form a blood conveying tube;

an external housing in communication with the blood conveying tube and an external balloon residing within the external housing;

a pressurization means for alternately pressurizing and applying vacuum to the external balloon, thereby alternately drawing blood and pumping blood to and from the external housing;

wherein the internal catheter is for placement within a left ventricle of the human and the external balloon is located outside of the patient;

wherein the pressurization means for alternately pressurizing and applying vacuum to the external balloon comprises a multiple stage pumping apparatus;

wherein the pressurization means comprises a dual action pumping apparatus having separate pumping sections for the internal retaining balloon and for the external balloon, thereby accommodating differing pumping requirements for the internal retaining balloon and the external inflation balloon; and wherein the external balloon is located within a relatively rigid housing and wherein the dual action pumping apparatus is capable of providing both positive pressure and vacuum to act upon the external inflation balloon located within the relatively rigid housing.

* * * * *